United States Patent [19]

Ajisaka et al.

[11] 4,377,512

[45] Mar. 22, 1983

[54] OXYGEN CARRIER FOR BLOOD SUBSTITUTE

[75] Inventors: Katsumi Ajisaka, Yokohama; Yuji Iwashita, Kawasaki, both of Japan

[73] Assignee: Ajinomoto Co., Inc., Tokyo, Japan

[21] Appl. No.: 277,950

[22] Filed: Jun. 26, 1981

[30] Foreign Application Priority Data

Jul. 2, 1980 [JP] Japan ................................ 55-90316

[51] Int. Cl.³ ............................................ C07G 7/00
[52] U.S. Cl. ...................... 260/112 B; 260/112.5 R; 424/101; 424/177
[58] Field of Search ...................... 260/112 B, 112.5 R

[56] References Cited

U.S. PATENT DOCUMENTS 4,001,200  1/1977  Bonsen et al. ............... 260/112.5 R
4,064,118  12/1977  Wong ............................ 260/112.5 R
4,330,463  5/1982  Luijerink ........................ 260/112 B

OTHER PUBLICATIONS

Biochemistry, vol. 11, No. 19, 1972, pp. 3576–3582, Benesch et al.
Chem. Abstracts, vol. 88, 1978, 79094g, Beez et al.

*Primary Examiner*—Howard E. Schain
*Attorney, Agent, or Firm*—Oblon, Fisher, Spivak, McClelland & Maier

[57] ABSTRACT

A hemoglobin modified by covalently bound inulin.

9 Claims, No Drawings

OXYGEN CARRIER FOR BLOOD SUBSTITUTE

BACKGROUND OF THE INVENTION

The present invention relates to a novel oxygen carrier, more particularly to hemoglobins covalently modified by inulin as an oxygen carrier for blood substitute.

SUMMARY OF THE INVENTION

An object of the present invention is to provide a compound capable of carrying oxygen which is useful as a substitute oxygen carrier in the bloodstream.

This object and other objects of the present invention as hereinafter will become more readily apparent can be attained by hemoglobin modified by covalently bound inulin.

DETAILED DESCRIPTION OF THE PREFERRED EMBODIMENTS

The heart of the present invention is the preparation of a hemoglobin based material in which the hemoglobin is modified by inulin. The prepared substance has excellent properties as a substitute for oxygen carriers in the blood. The substitute oxygen carrier of the present invention has the following characteristics:
  (1) When it is infused into a subject, the residence time in the bloodstream is long enough so that it is acceptable as a substitute oxygen carrier in the blood.
  (2) It has the ability to supply oxygen to tissues.
  (3) It is easily metabolised and does not accumulate in the body.
  (4) It is a nontoxic material.
  (5) It not only carries oxygen but also works as a plasma expander.

The hemoglobin used in the present invention includes hemoglobin material obtained from animals such as cattle, swine, sheep, horses, dogs, monkeys and chickens, as well as human beings. Suitable hemoglobin material also includes hemoglobin derivatives such as sugar, nucleotide, alcohol, carboxylic acid, or derivatives of sulphate such as pyridoxal-5′-sulphate, or phosphate such as pyridoxal-5′-phosphate derivative of hemoglobin.

The inulin used in the present invention preferably has a molecular weight in the range of 4,000 to 6,000 daltons, and its molecular structure may be branched.

Various methods can be utilized for combining inulin with hemoglobin. For instance, the amino group of the hemoglobin can be coupled to the hydroxy group of inulin by a coupling agent such as cyanogen bromide, or by a polyfunctional crosslinking agent such as cyanuric chloride, 2,2′-dichlorobenzidine, p,p′-difluoro-m,m-dinitrodiphenylsulfone, 2,4-dichloronitrobenzene or the like.

In another example inulin can be combined with hemoglobin using a dicarboxylic acid such as succinic acid, glutaric acid, or adipic acid as a linking agent. That is, inulin is first esterified by one of these dicarboxylic acids, preferably an anhydride thereof, and then the free carboxyl group of the dicarboxylic acid monoester after activation by a typical carboxyl group activating agent such as N-hydroxy succinimide, pentachlorophenol, succinimide, carbodiimidazole, or imidazole, is combined with hemoglobin.

In the instance a hemoglobin derivative is used as a starting material, the same reaction procedure can be applied. For example, pyridoxal phosphate is initially coupled to hemoglobin by the method described by R. E. Benesch, R, Benesch, R. D. Renthal, and N. Maeda, in *Biochemistry*, 11, 3675 (1972). Next, inulin is combined with the hemoglobin derivative by the method described above.

In the synthesis of the modified hemoglobin for the present invention, from 1 to about 20 molecules of inulin can be attached to a given hemoglobin subunit. However, a consideration of some importance is that a material which is to be used as an oxygen carrier in the blood stream cannot be so large that it raises the viscosity of the blood stream to an unacceptably high level. From this viewpoint, the preferred number of inulin molecules attached to a subunit of hemoglobin usually ranges from 1 to about 15.

Having generally described this invention, a further understanding can be obtained by reference to certain specific examples which are provided herein for purposes of illustration only and are not intended to be limiting unless otherwise specified.

EXAMPLE 1

Inulin (10 g, 0.002 mole, Tokyo Kasei Co., Tokyo) was dissolved in 100 ml water and to this solution cyanogen bromide (1 g, 0.01 mole) in dioxane solution (10 ml) was added dropwise at ice temperature. During the reaction, the pH of the mixture was maintained between 9 and 10 by addition of 2 N NaOH solution.

After the addition of cyanogen bromide was completed (30 min.), the mixture was stirred for 20 min.

The reaction mixture was poured into cold acetone (400 ml) and the activated inulin was obtained as a suspension. This suspension was allowed to stand for several minutes, and then the supernatant was removed by decantation. The unreacted cyanogen bromide was removed by washing with cold acetone (300 ml). After the complete removal of the remaining acetone, an aqueous solution (50 ml) containing stroma free hemoglobin (5.2 g, 0.08 mmole) was added. The mixture obtained was stirred for 4 hours at 4° C.

The mixture was ultrafiltered and concentrated by a membrane "XM-100" (Amicon Co., USA).

In order to determine the relationship between the residence time in the bloodstream and the molecular weight of the substance of the present invention, a higher molecular weight fraction and a lower molecular weight fraction of the hemoglobin modified by covalently bound inulin (about equal amounts) were separated by gel permeation chromatography on "Sephadex G 100" (Pharmacea Co., Sweden). Hereinafter, these two fractions are called "Inulin-Hb 1" and "Inulin-Hb 2".

The number of inulin molecules which combine with one subunit of hemoglobin was determined as follows:

The solution of inulin-combined hemoglobin, whose volume is indicated as $V_o$ and whose hemoglobin concentration is shown as $C_o$ (from the cyanomethemoglobin method), was lyophilized and its dry weight was measured. The number (n) of inulin molecules which are combined with one hemoglobin subunit is obtained by the following equation.

$$n = \frac{(m_o - C_oV_o)/M_I}{C_oV_o/M_H}$$

In this equation, $M_I$ is the average molecular weight of the inulin used, and $M_H$ is the molecular weight of the hemoglobin subunit, and $m_o$ is the net weight of the inulin combined hemoglobin after lyophilization.

The molecular weight (M) of an inulin-combined hemoglobin subunit can be expressed by the following equation.

$$M = M_H + n M_I$$

The number of the combined inulin molecules and the molecular weight of the substance obtained by this method are shown in Table 1.

TABLE 1

| Substance | Number of Combined* Inulin Units | Molecular Weight* |
|---|---|---|
| Inulin-Hb 1 | 1.7 | $2.5 \times 10^4$ |
| Inulin-Hb 2 | 6.8 | $5.1 \times 10^4$ |

*The "Number of Combined Inulin Units" and "Molecular Weight" are defined as one subunit in the specification.

EXAMPLE 2

To a 100 ml inulin solution containing 5 g (0.001 mole) of inulin, 1 gram (0.001 mole) of cyanuric chloride in admixture with 10 ml water and 20 ml acetone, was added dropwise. During the reaction the pH of the reaction mixture was maintained between 10 and 11 by addition of 2 N NaOH solution. The mixture was stirred for 5 minutes after completing the addition, and then the pH was adjusted to 3 by addition of 2 N HCl solution. The reaction mixture was poured into 500 ml acetone and the obtained precipitate was collected by filtration and washed by acetone and dried. The product was dissolved in 100 ml 0.2 M borate buffer and then 5.6% stroma free hemoglobin solution (15 ml) was added. The mixture was stirred for 3 hours in an ice bath. The reaction mixture was treated by the procedure described in Example 1. Two fractions "Inulin-Hb 3" and "Inulin-Hb 4" were prepared by gel permeation chromatography as described in Example 1.

The number of inulin molecules in the inulin-combined hemoglobins was determined by the same method described in Example 1. The estimated average molecular weight values found are given in Table 2.

TABLE 2

| Substance | Number of Combined Inulin Units | Molecular Weight |
|---|---|---|
| Inulin-Hb 3 | 3.9 | $3.6 \times 10^4$ |
| Inulin-Hb 4 | 7.4 | $5.4 \times 10^4$ |

EXAMPLE 3

Instead of the stroma free hemoglobin solution in Example 2, a 6.3% aqueous solution of pyridoxylated hemoglobin (13.3 ml) was employed and the procedure described in Example 2 was repeated. "Inulin-Hb 5" was obtained upon concentration of the reaction mixture through a membrane "XM-100" (Amicon Co., USA).

The number of combined inulin molecules per one subunit of hemoglobin in the "Inulin-Hb 5" fraction was 4.2 and the molecular weight of the product was found to be $3.7 \times 10^4$.

EXAMPLE 4

Inulin (5.4 g, 0.03 mole) and succinic anhydride (3.0 g, 0.03 mole) were dissolved in pyridine (50 ml) and the solution was refluxed for two hours. Then n-hexane (200 ml) was added to the solution and the precipitate was filtered and washed with n-hexane. The precipitate (2.8 g), N-hydroxysuccinimide (2.4 g, 0.021 mole), and dicyclohexylcarbodiimide (4.2 g, 0.021 mole) were dissolved in 60 ml N,N-dimethylformamide and the reaction solution was refluxed for one hour. After removing the dicyclohexylurea by filtration, n-hexane (300 ml) was added to the filtrate.

The precipitate of activated inulin was filtered and washed with n-hexane. The activated inulin 2.1 g (0.0004 mole) was added to the 1% hemoglobin solution (100 ml, 0.000016 mole) buffered by 0.2 M borate buffer (pH 8.5). The reaction mixture was stirred for 16 hours at 4° C., ultrafiltered, and concentrated by the membrane "PM-30" (Amicon Co., USA).

The obtained product "Inulin-Hb 6" was composed of three inulin molecules per one subunit of hemoglobin and its molecular weight was found to be $3.1 \times 10^4$.

EXAMPLE 5

A one percent solution of pyridoxylated hemoglobin in 0.2 M borate buffer (100 ml, 0.000016 mole) was used instead of unmodified hemoglobin for the reaction with the activated inulin as described in Example 4. The obtained substance "Inulin-Hb 7" was found to have 2.5 inulin molecules combined with one subunit of hemoglobin and the molecular weight was found to be $2.9 \times 10^4$.

The half residence time (T-50) of the various obtained fractions in the circulation of rats was determined as follows. Male Spaque Dawley rats (200–300 g) were anesthetized by the ip injection of 400 mg/kg pentobarbital. After the phlebotomy of 5 ml/kg blood through a polyethylene catheter inserted in the femoral vein, the same volume of a hemoglobin or Inulin-combined hemoglobin solution (concentration 4–6%) was infused through the same catheter. Aliquots (0.5 ml) of the blood were collected at 5, 10, 30, 60, 90 and 120 minutes after the infusion and then the concentration of the derivatives injected into the plasma was measured by the cyanomethemoglobin method after centrifugation. The half residence time for each sample was obtained by semilogarithmic plots of concentration against the time after each infusion.

The results are given in Table 3.

TABLE 3

| Substance | Half Residence Time (minute) | $P_{50}$ Value* (mm Hg) |
|---|---|---|
| Inulin-Hb 1 | 90 | 2.05 |
| Inulin-Hb 2 | 110 | 1.46 |
| Inulin-Hb 3 | 110 | 0.94 |
| Inulin-Hb 4 | 120 | 0.72 |
| Inulin-Hb 5 | 100 | 1.25 |
| Inulin-Hb 6 | 90 | 3.85 |
| Inulin-Hb 7 | 80 | 4.40 |
| Hemoglobin (control) | 40 | 6.60 |
| Dextran-Hb (control) | 70 | 1.20 |

*25° C., 0.1 M NaCl solution, pH 7.4.

The oxygen dissociation curve of each tested inulin-combined hemoglobin sample was measured by an apparatus constructed as described by K. Imai, H. Morimoto, M. Kotani, H. Watari, H. Waka, and M. Kuroda in *Biochim. Biophys. Acta*, 200, 189–196 (1970).

The values of $P_{50}$, at which pressure half of the oxygen coordinated to the hemoglobin derivative is released, were estimated for each sample from the dissociation curves and these values are shown in Table 3.

A dextran-hemoglobin complex (molecular weight: over $2.0 \times 10^5$) shown in Table 3 as a reference substance, was prepared by combining dextran (molecular weight: $1.6 \times 10^5$) with hemoglobin using cyanuric chloride to facilitate bonding of the dextran to the hemoglobin.

From the results obtained the half residence time for the circulation of each inulin-combined hemoglobin fraction tested was much longer than that of hemoglobin itself. Moreover, these substances have a noteworthy ability to supply sufficient oxygen to the tissues of the body. Furthermore, the inulin-combined hemoglobin fractions are good plasma expanders. Therefore, these substances are very useful as substitute oxygen carriers in the blood.

Having now fully described the invention, it will be apparent to one of ordinary skill in the art that many changes and modifications can be made thereto without departing from the spirit or scope of the invention as set forth herein.

What is claimed is:

1. A hemoglobin modified by covalently bound inulin.

2. The compound of claim 1, wherein said hemoglobin is obtained from cattle, swine, sheep, horses, dogs, monkeys, chickens or human beings.

3. The compound of claim 1, wherein the hemoglobin component of said modified hemoglobin is a sugar nucleotide, alcohol, carboxylic acid, sulphate or phosphate derivative of hemoglobin.

4. The compound of claim 1, wherein the inulin component of said modified hemoglobin has a molecular weight of 4,000 to 6,000 daltons.

5. The compound of claim 1, wherein said compound comprises from 1 to 20 inulin units attached to one hemoglobin subunit.

6. The compound of claim 5, wherein the number of inulin units combined with one hemoglobin subunit ranges from 1 to 15.

7. A method of preparing hemoglobin modified by covalently bound inulin, comprising:
coupling inulin units via hydroxyl groups thereon to amino groups on a hemoglobin subunit by a coupling agent selected from the group consisting of cyanogen bromide, cyanuric chloride, 2,2-dichlorobenzidine, p,p'-difluoro-m,m'-dinitrodiphenylsulfone or 2,4-dichloronitrobenzene.

8. A method of preparing hemoglobin modified by covalently bound inulin, comprising:
esterifying inulin with a dicarboxylic acid, and reacting the remaining free carboxyl group of the partially reacted dicarboxylic acid with hemoglobin.

9. The compound of claim 1, wherein the hemoglobin component of said modified hemoglobin is a pyridoxal-5'-phosphate or pyridoxal-5'-sulphate derivative of hemoglobin.

* * * * *